Figure 1:
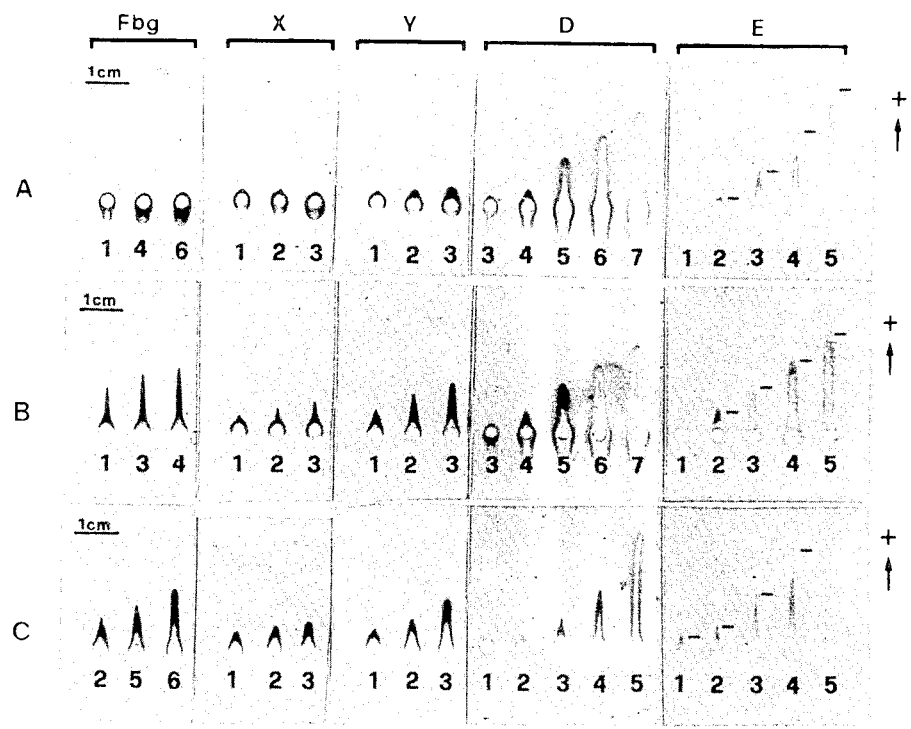

United States Patent [19]

Fabrizi et al.

[11] Patent Number: 4,666,864
[45] Date of Patent: May 19, 1987

[54] GEL COMPOSITION FOR DETERMINING THE FIBRINOGEN CONTENT IN PLASMA BY ELECTROIMMUNODIFFUSION

[75] Inventors: Paolo Fabrizi, Monteriggioni; Alessandro Provvedi, Siena; Paolo Tarli, Monteriggioni, all of Italy

[73] Assignee: Sclavo, S.p.A., Milan, Italy

[21] Appl. No.: 575,443

[22] Filed: Jan. 31, 1984

[30] Foreign Application Priority Data

Feb. 8, 1983 [IT] Italy ............................. 19461 A/83

[51] Int. Cl.⁴ ..................... C25B 7/00; G01N 33/558; G01N 33/559; G01N 33/86
[52] U.S. Cl. .................................. 436/516; 204/182.8; 435/13; 436/514; 436/515; 436/69; 530/382
[58] Field of Search .................. 204/180 G; 436/516, 436/514, 515, 69; 536/21; 435/13; 530/382

[56] References Cited

FOREIGN PATENT DOCUMENTS 0107585 8/1979 Japan ...................................... 536/21

OTHER PUBLICATIONS

Nielson, et al., Clinica Chimica Acta, vol. 35, (1971), pp. 281-284.
Farrell, et al., J. Immunol. Methods, vol. 1, (1972), pp. 217-229.
Schmid, P., Clinica Chimica Acta, vol. 26, (1969), pp. 183-184.
Laurell, C., Anal. Biochem., vol. 15, (1966), pp. 45-52.
Laurell, et al., Methods in Enzymology, vol. 73, (1981), pp. 339-369.
Weeke, B., Scand. J. Clin. Lab. Invest., vol. 21, (1968), pp. 351-354.
Jaqves, L. B., Science, vol. 206, (1979), pp. 528-533.
McGilvery, R. W.; Biochemistry, a Functional Approach, 1979, W. B. Saunders Co., pp. 183-186.
Plate, et al., Thrombosis Research, vol. 27, (1982), pp. 131-141.

Primary Examiner—Robert J. Warden
Assistant Examiner—Stephen C. Wieder
Attorney, Agent, or Firm—Hedman, Gibson, Costigan & Hoare

[57] ABSTRACT

A composition for determining the fibrinogen content in plasma by electroimmunodiffusion, said composition essentially comprising heparin and agarose.

1 Claim, 3 Drawing Figures

GEL COMPOSITION FOR DETERMINING THE FIBRINOGEN CONTENT IN PLASMA BY ELECTROIMMUNODIFFUSION

Fibrinogen is a plasmatic glycoprotein which plays a leading role in the coagulative and fibrinolytic system as well as in the adjustment of the viscosity of blood. As a matter of fact, fibrinogen, in addition to being the physiological substrate of both thrombin and plasmin, which are the enzymes responsible for the formation of the fibrin clot and the lysis of both fibrinogen and fibrin, respectively, is, by virtue of its form and molecular size (frictional ratio 2.34 Mol. wt 340,000) and due to its property of encouraging red cell aggregation, an important viscosity-adjustment factor and thus a regulator of the blood flow and the oxygen-carrying.

An increase of the plasmatic concentration of fibrinogen, which is usually comprised between 200 and 400 mg/dl, is experienced, as a rule in those situations, such as pregnancy, post-operatory periods, rheumatoid arthritis and others, in which the "acute-stage proteins" increase and is a hazardous factor due to the onset of hypercoagulability states.

A decrease of the fibrinogen blood level, conversely, is experienced in the case of acquired diseases, such as liver diseases, disseminated intravascular coagulation, hyperfibrinolysis and others, and of congenital diseases, such as afibrinogenaemia, constitutional hypofibrinogenaemia and like conditions, and may give rise to haemorragic clinical patterns.

In hyperfibrinolytic states, fibrinogen and fibrin (if any) are digested by the action of the plasmin which is formed as a result of the activation of plasminogen by exogenous activators, such as streptokinase, urokinase and the like, or by endogenous activators, so that they are converted into degradation products of disparate molecular weights such as: X(mol wt 240,000), Y(mol wt 155,000), D(mol wt 83,000) and E(mol wt 50,000). The pathological concentrations of such fragments generally range from 10 μg/ml and 250 μg/ml, but even higher values than that may be attained.

The FDP's, that is the Fibrinogen Degradation Products, possess characteristic properties of their own, viz.:
they inhibit, especially the X and the Y products, thrombin and the polymerization of the fibrin monomers (an anticoagulant activity);
the Y, D and E fragments cannot be coagulated by thrombin;
they form soluble complexes with the fibrin monomers (anticoagulant activity);
the D and E fragments have different antigenic properties;
they have a higher anodic mobility and a higher diffusibility (fragments D and E) than fibrinogen in an agarose gel, and have characteristics which are common to the native molecule;
they retain a few antigenic determinants of fibrinogen so that they react with antifibrinogenic sera;
the X fragment is coagulated by thrombin.

The FDP's, which, in the hyperfibrinolytic states contribute, due to their anticoagulant activity, towards aggravating the coagulation defect as originated by hypofibrinogenaemia, are interfering factors whenever fibrinogen is to be determined both biologically and immunologically.

Fibrinogen in plasma is usually metered by coagulation procedures which exploit its coagulation ability under the action of thrombin (Thrombin time method, see Clauss, A. Acta Haematol., (Basel), 17, 237–246, (1957)), or by immunoprecipitation methods which exploit its antigenic properties, such as method of radial immunodiffusion (Chen, T., and Lai, C. H., Ann. J. Clin. Pathol., 52, 629–630, (1969), electroimmunodiffusion methods (Nielsen, H. G., and Weeke, B., Clin. Chim. Acta, 35, 281–284, (1971), and nephelometric methods (Farrel, G. W., and Wolfe, P., J. Immunol. Methods, 1, 217–229 (1972).

Both these kinds of procedures are affected by the presence of the FDP's. As a matter of fact, the biological methods, which are based on the inverse correlation existing between the fibrinogen concentration and the coagulation time, exhibit, due to the anticoagulant activity of the FDP's, a tendency towards underrating, whereas the immunologic methods tend to overestimate because the antifibrinogenic serum reacts with the FDP's also.

The immunoprecipitation in gel methods are adopted as an alternative to the coagulation method, or comparatively with respect to same, in order to make possible functional defects of the fibrinogen molecule conspicuous (disfibrinogenaemia and the like). From among the latter methods, electroimmunodiffusion according to Laurell (Nielsen, H. G., and Weeke, B. Clin. Chim. Acta, 35, 281–284; (1971) is preferred due to its rapidity over the radial immunodiffusion since the latter, as a consequence of the low fibrinogen diffusion velocity, requires outstandingly long diffusion times (at least 5 days) (see Schmid, P., Clin. Chim. Acta, 26, 183–184, (1969), and Brittin, G. M., Rafinia, H. Raval, D., Werner, M., and Brown, B., Clin. Chem., 17, 639, (1971).

The electroimmunodiffusion method according to Laurell (Laurell, C. B., Anal. Biochem., 15, 45–52, (1966)—Laurell, C. B. and McKay, E. J., Methods in Enzymology, Immunochemical Techniques, Part B (Langone, J. J. and Von Vunakis, M. Eds.) Vol. 73, 339–369 (1982), Academic Press, New York), consists in inseminating constant volumes of antigens in wells formed through an agarose gel which contains the corresponding antibody (IgG). The antigen is then caused to migrate in an electric field, from the negative pole (cathode) to the positive one (anode). Under alkaline pH conditions (from 8.2 to 8.9) the anodic migration of the antigen is braked by the flow in the contrary direction of the specific IgG's and the anodic migration of these latter is counterbalanced by the electroendoosmotic flow.

Under these conditions, if the anodic mobility of the antigen proves adequate, spirelike immunoprecipitate peaks ("rockets") are formed, the height of which is proportional to the antigen concentration.

The fibrinogen molecule, due both to its charge (isoelectric point 5.5) and its elongate configuration (frictional ratio 2.34) has a scanty electrophoretic mobility ($\beta_2$ globulin) so that, in order to be able to determine fibrinogen with an adequate accuracy with the electroimmuno diffusion method, its anodic mobility must be improved.

The method which is routinely used to this purpose (Nielsen, H. G. and Weeke, B., Clin. Chim. Acta, 35, 281–284, (1971)), consists in having the plasma being tested reacting with an equal volume of double-molar KCNO for 30 mins. at 37° C. KCNO is capable of binding itself to the α- and ε-amine groups of the proteins to form stable compounds according to the following carbamylation reaction pattern:

protein—NH$_2$+NCO$^-$ (pH over 6)→protein—NHCONH$_2$

Replacing the amine groups by carbamylaamine groups, which are less basic in character, lowers the isoelectric point of fibrinogen and of other plasmatic protein, so that their overall mobility is improved (Weeke, B., Scandi. J. Clin. Lab. Invest., 21, 351–354, (1968)). In the case of fibrinogen, the electrophoretic mobility passes from β to α (Nielsen, H. G. and Weeke, B., Clin. Chim. Acta, 35, 281–284, (1971)).

We have now found that, by adding commercial sodium heparin to agarose, it becomes possible to meter fibrinogen in plasma samples by electroimmunodiffusion withouth carrying out the carbamylation reaction.

Commercial heparin is a polydispersion of polysaccharides having a molecular weight in the range of from 6,000 to 30,000 and the monosaccharide units, as represented by the uronic acids (α-L-iduronic and β-D-glucuronic acids) and α-D-glucosamine, are bonded by 1,4-glycoside bonds according to the sequential pattern reported below:

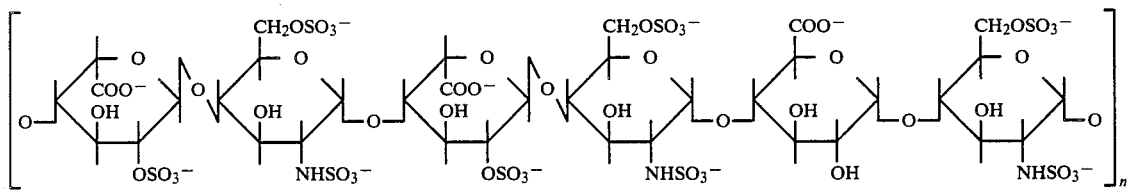

The polyanionic properties impart to this polysaccharide the capability of forming complexes with a number of basic, amphoteric substances and with cations. More particularly, heparine is bonded to fibrinogen (Jaques, L. B., Science, 206, 528–533, (1979) and Plate, N. A. and Valnev, L. J., Thrombosis Res., 27, 131–141, (1982)) and exhibits the property of reducing both the viscosity and the stiffness of fibrinogen (King, R. G. and Copley, A. L., Biorheology, 15, 461, (1978)), and, according to applicants' observation, by adding heparin to agarose, the anodic mobility of fibrinogen and of the X and Y fragments is increased to a higher and to an equal degree relative to carbamylation with potassium cyanate, respectively, but without altering the mobility of the low molecular weight fibrinogen fragments D and E, said latter mobility being, conversely, increased by the carbamylation reaction. Therefore, in the measurement of fibrinogen by EID (electroimmunodiffusion) in plasma samples which contain pathological amounts of FDP's, the carbamylation with cyanate enhances the sensitivity to FDP's by increasing their anodic mobility, so that the overestimation of fibrinogen may be further exalted, due to the immunoreactivity of FDP's against fibrinogen antibodies.

Thus, a primary object of the present invention is to provide a composition which makes possible the determination of fibrinogen by EID (electroimmunodiffusion), said composition essentially consisting of agarose which has been supplemented with 35–45 g (grams) of heparin per 100 g of agarose, corresponding to from 35% to 45% by weight.

This invention also relates to the use of the composition defined above for the identification of fibrinogen by EID.

The procedure followed by us for determining fibrinogen by EID (electroimmunodiffusion) can be summarized as follows: a 1%-agarose solution is prepared by dissolving commercial agarose having average electroendoosmotic properties and a sulphate content of less than 0.35%, in a boiling electrophoresis buffer Tris 0.356-molar, Na$_2$-EDTA 0.010-molar, boric acid 0.356-molar, pH 8.2, to which 1% of NaN$_3$ has been added. A specific antifibrinogen serum as obtained from rabbits, and a solution of commercial sodium heparin (the specific anticoagulant activity of commercial heparins is generally around 150 UI/mg) at a concentration of 100 mg/ml (heparinized gel), or distilled water (carbamylated samples) are added to the agarose solution which has been cooled to 50° C., in such an amount as to have a final concentration of 21.5 μl/ml and 43 μl/ml, respectively. These mixtures, maintained at 50° C., are layered on a polyester film 94×84×0.2 mm, with a volume to surface ratio of 144 μl/cm$^2$.

Upon gelling, the plates are allowed to stand 20 minutes at room temperature, whereupon, in the central zone of the gel, there is formed an aligned set of wells having a diameter of 3 mm and the well centres are spaced 10 mm apart from each other.

The samples, diluted in the electrophoresis buffer adjusted to a pH of 7.4, are inseminated in the wells by a microsyringe having a volume of 10 μl. Electrophoresis is now carried out in a water-cooled cell maintained at 15° C., by applying an electric field to 70 V/cm during one hour. On completion of electrophoresis, the gels are washed with NaCl (0.15-molar), covered with several layers of filter paper, subjected to a pressure of 15 g/cm$^2$ for 15 minutes, dried in oven, stained with a 0.5% (weight/volume) solution of Coomassie Brilliant Blue R-250, decolorized and allowed to dry in air. The heights of the peaks (distance between the center of the well and the peak point), is measured in mm with a sliding gauge.

Figure 2:
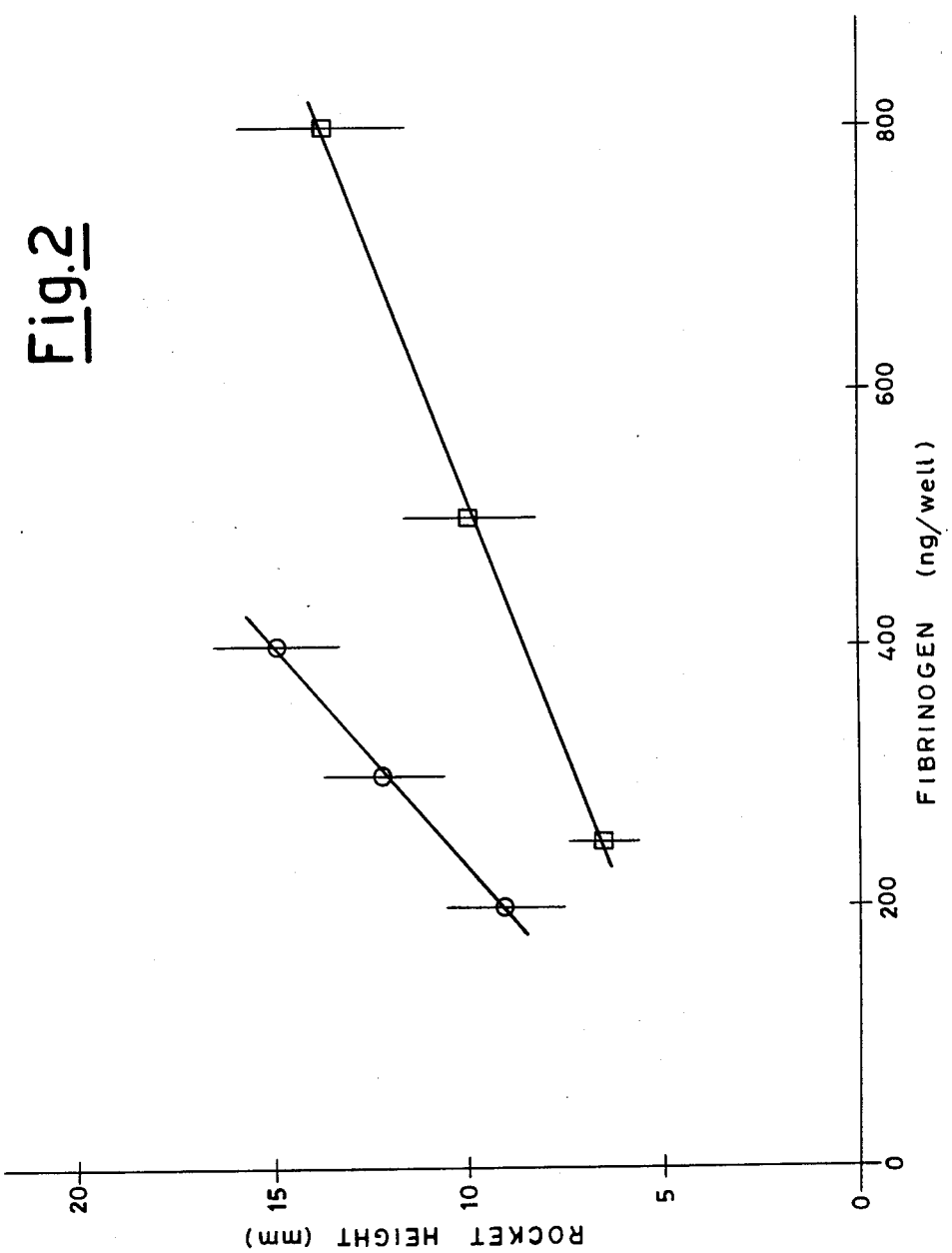

In the determination of the plasmatic fibrinogen by EID, the heparinized agarose affords, as compared with the carbamylation of the samples, the following advantages:

Sensitivity is improved: The EID/HP (electroimmunodiffusion on a heparinized agarose gel) is nearly twice as sensitive to fibrinogen as EID/KCNO (electroimmunodiffusion with carbamylated samples). As a matter of fact, the detection limit of fibrinogen, as calculated by regression equations of standard curves for a 6-mm high precipitin rocket, was found to be 95 ng/well and 210 ng/well, when using EID/HP assay method and EID/KCNO assay method, respectively. (FIG. 2 of the accompanying drawings shows the standard curves of fibrinogen as obtained with the EID/HP method ($y=3.19+0.29x$; $r=0.956$) and the EID/KCNO method ($y=3.24+0.13x$; $r=0.964$). Symbols are small circles (o) and small squares (□), respectively.

Each curve has been derived from 10 curves as obtained in different days. The vertical small bars show the standard deviation. The equations of the regression straight line have been reported in brackets (y=segment intercepted on the ordinate axis+slope x) and r is the correlation coefficient).

Specificity is improved: Agarose heparinization does not affect the sensitivity to the D and E fragments (purified preparations) while, conversely, it enhances the sensitivity to the X and Y FDP fragments (purified preparations) to the same extent as for sample carbamylation. Sample carbamylation, on the contrary, exalts the sensitivity to the D and E fragments so that the detection limit is lowered from 300 ng/well to 100 ng/well for fragment D, and from 10 ng/well to 5 ng/well for the E fragment.

FIG. 1 shows the influence of agarose heparinization upon the quantitation of plasma fibrinogen and purified FDP by EID. Gel B contains heparin. Gels A and C have no heparin. The samples added to the wells of gel C had previously been carbamylated. The wells marked Fbg 1 to 6 contain 200 ng, 250 ng, 300 ng, 400 ng, 500 ng and 800 ng of fibrinogen, respectively. The wells marked X 1 to 3 contain 200 ng, 300 ng and 400 ng of fragment X, respectively. The wells marked Y from 1 to 3 contain 150 ng, 300 ng and 600 ng of fragment Y, respectively. The wells marked D from 1 to 7 contain 0.1 ng, 0.3 ng, 1 ng, 3 ng, 10 ng, 30 ng and $100.10^2$ ng of fragment D, respectively. The wells marked with E from 1 to 5 contain 5 ng, 10 ng, 20 ng, 40 ng and 80 ng of fragment E, respectively.

Table I tabulates the values of fibrinogen as reported by EID/HP and EID/KCNO assays in an abnormal FDP-containing plasma, which had artificially been prepared by digesting a fibrinogen/plasminogen solution with streptokinase.

Table I thus shows that, when undigested fibrinogen is added to plasma, both assay methods give the expected value for fibrinogen, namely: the average for plasma (264 mg/dl) plus the added fibrinogen (500 mg/dl).

As the added fibrinogen is digested, the fibrinogen level as quantitated by both electroimmunoassays should be decreased and outh to approach the value of 132 mg/dl. The EID/HP assay actually gives the forecast value, whereas the EID/KCNO assay gives a much higher level, since, when FDP are present, and this is especially true for the low molecular weights FDP's, as these latter appear in digested fibrinogen after a digestion time of 15 minutes approx., the EID/KCNO assay tends to overrun.

Thus, the fibrinogen value as determined with the EID/KCNO procedure after 120 minutes overrun the correct result by 40% approximately. This fact is a clear indication that the EID/HP assay procedure according to this invention electively detects the intact fibrinogen because this assay as a whole is virtually insensitive to the tested FDP concentration (this is about 250 μg/ml) as a consequence of two determining factors, viz.:

(1) Its reduced sensitivity to the D and E fragments, and (2) Its improved sensitivity to fibrinogen as such, that which enables the determination to be carried out in thinner plasma samples.

Moreover, results which did not significantly deviate from the tests tabulated in Table I, were obtained when repeating the tests with normal plasma, to which fibrin monomers had been added beforehand in an amount of 100 μg/ml. Such fibrin monomers had been prepared from human fibrinogen and checked according to the accepted methods, such as Protasi, O., Fabrizi, P., Antoni, G. and Neri, P., Thrombosis Res., 25, 149–153 (1982).

Figure 3:
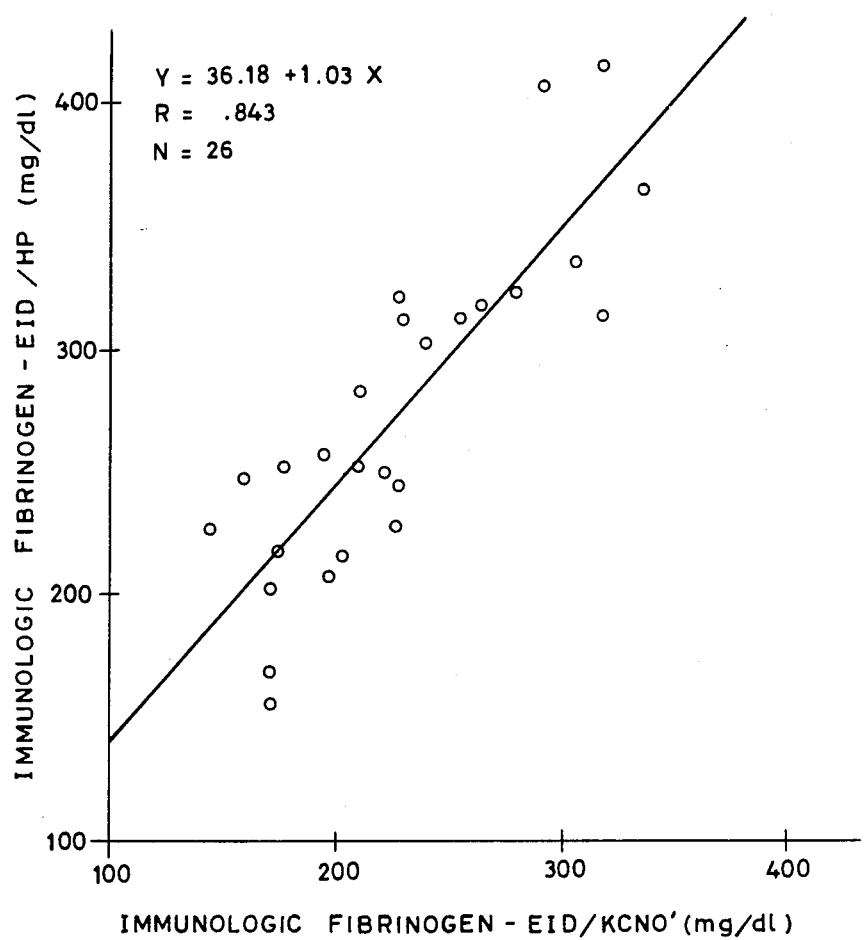

Analysis times are reduced: fibrinogen, in fact, can be quantitated without previously treating plasma. Fibrinogen values of normal plasma samples, as determined by EID/HP assay and EID/KCNO assay and the Clauss coagulative method did not show any significant difference: as a matter of fact the ordinate intercept and the slope of the regression straight lines do not differ, with 95% probability, from 0 and from 1, respectively and, when analysis for linear regression is made, a significant correlation has been observed between the two immunological methods. In FIG. 3 of the accompanying drawings, the comparison is reported between the fibrinogen values determined by EID/KCNO (abscissa, x) and those determined by EID/HP (ordinate, y). The Figure reports also the equation of the regression line, the correlation coefficient, called R in this particular case, and the number of tested plasma samples, N. It has also been seen that there are no significant differences between the two immunological methods aforementioned and the coagulative method (EID/HP assay: $y=7.85+1.08x$; $R=0.869$; $N=26$. For the EID/KCNO assay it is: $y=9.65+0.89x$; $R=0.881$ and $N=26$.

It can thus safely be concluded that the use of heparin included in an agarose gel, instead of using the carbamylated samples, in order to improve the fibrinogen anodic mobility, renders specific (only intact fibrinogen is determined, in fact) and more sensitive (sensitivity is more than doubled) and more rapid (sample pre-treatment can be dispensed with), the determination of fibrinogen by EID both in normal plasma and in abnormal plasma which contains fibrin nonomers or FDP's, or both.

This invention thus also relates to a gel composition which makes possible the determination of a fibrinogen by electroimmunodiffusion. Such a gel is obtained by gelling a buffer solution of a pH of 8.2 (Tris(hydroxymethyl)aminomethane 0.010-molar, boric acid 0.356-molar, and sodium azide 1 g/l), said gel containing 4.3 g of sodium heparin (corresponding to 645 IU of anticoagulating activity) and 10 g of agarose per liter.

This invention also relates to the use of the composition reported above in the identification of fibrinogen by electroimmunodiffusion and by immunoelectrophoresis.

TABLE I

| Abnormal plasma samples[a] | Fibrinogen (mg/dl)[b] | |
|---|---|---|
| | EID/HP | EID/KCNO |
| A | 380 | 375 |
| | (395–350) | (388–361) |
| B | 367 | 376 |
| | (387–348) | (391–366) |
| C | 277 | 368 |
| | (344–248) | (389–360) |
| F | 198 | 327 |
| | (225–175) | (351–307) |
| G | 167 | 294 |
| | (184–156) | (327–263) |

[a]Prepared by mixing six normal plasmas (average concentration of clottable fibrinogen is 264 mg/dl) with an equal volume of undigested fibrinogen/plasminogen solution (clottable fibrinogen: 500 mg/dl) to obtain sample A. Sample B is obtained by digesting sample A or 15 minutes with streptokinase, sample C is obtained by a digestion of 30 minutes, sample F after a digestion of 60 minutes and sample G after a digestion as long as 120 minutes. At all the selected degradation times, the FDP levels of the digested fibrinogen solutions remained comparatively constant and ranged from 403 μg/ml to 508 μg/ml.
[b]The results are expressed as arithmetic means, the range of variation being bracketed.

(a) Prepared by mixing six normal plasmas (average concentration of clottable fibrinogen is 264 mg/dl) with an equal volume of undigested fibrinogen/plasminogen solution (clottable fibrinogen: 500 mg/dl) to obtain sample A. Sample B is obtained by digesting sample A for 15 minutes with streptokinase, sample C is obtained by a digestion of 30 minutes, sample F after a digestion of 60 minutes and sample G after a digestion as long as 120 minutes. At all the selected degradation times, the FDP levels of the digested fibrinogen solutions remained comparatively constant and ranged from 403 µg/ml to 508 µg/ml. (b) The results are expressed as arithmetic means, the range of variation being bracketed.

We claim:

1. A method for assaying fibrinogen in a composition comprising, applying a sample containing fibrinogen to an electromorphoresis medium agarose and assaying by by electroimmunodiffusion, wherein the improvement comprises using as the electrophoresis medium agarose to which has been added 35% to 45% by weight of heparin, based on the weight of the agarose.

* * * * *